(12) United States Patent
Gelissen et al.

(10) Patent No.: US 12,622,621 B2
(45) Date of Patent: *May 12, 2026

(54) DRY ELECTRODES FOR ELECTROPHYSIOLOGY MEASUREMENT

(71) Applicant: Nederlandse Organisatie voor toegepast-natuurwetenschappelijk onderzoek TNO, The Hague (NL)

(72) Inventors: Jozef Hubertus Gelissen, Eindhoven (NL); Charlotte Kjellander, Eindhoven (NL); Panditha Pradeep, Eindhoven (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 104 days.

This patent is subject to a terminal disclaimer.

(21) Appl. No.: 18/118,168

(22) Filed: Mar. 7, 2023

(65) Prior Publication Data

US 2023/0284953 A1 Sep. 14, 2023

Related U.S. Application Data

(63) Continuation of application No. 17/689,072, filed on Mar. 8, 2022, now abandoned.

(30) Foreign Application Priority Data

Mar. 23, 2022 (EP) ..................................... 22163886

(51) Int. Cl.
*A61B 5/263* (2021.01)

(52) U.S. Cl.
CPC .................................... *A61B 5/263* (2021.01)

(58) Field of Classification Search
CPC ......... A61B 5/263; A61B 5/276; A61B 5/257; A61B 5/25; A61B 5/27; A61B 5/28; A61B 5/274
See application file for complete search history.

(56) References Cited

U.S. PATENT DOCUMENTS 5,732,699 A * 3/1998 Lundback ............. B25B 11/005
600/387
8,792,957 B2 7/2014 Greene
(Continued)

FOREIGN PATENT DOCUMENTS

JP 52162089 * 12/1977

OTHER PUBLICATIONS

Sinnaeve A, Willems R, Backers J, Holovoet G, Stroobandt R. Pacing and sensing: how can one electrode fulfill both requirements? Pacing Clin Electrophysiol. May 1987; 10(3 Pt 1):546-54. doi: 10.1111/j. 1540-8159.1987.tb04519.x. PMID: 2440005. (Year: 1987).*

*Primary Examiner* — Linda C Dvorak
*Assistant Examiner* — William Mossbrook
(74) *Attorney, Agent, or Firm* — Leydig, Voit & Mayer, Ltd.

(57) ABSTRACT

Apparatuses for making electrical connections in electrophysiological measurements and monitoring are disclosed. One such apparatus includes a first side having an electrical contact; a second side opposing the first side and having an electrode disposed over the second side; and a layer disposed between the first side and the second side. The layer is adapted to remove moisture from a region around the electrode. The apparatus also has an electrode line in electrical contact with the electrode disposed over the layer on (Continued)

the first side and extending over the layer on the second side. The electrode line is electrically connected to the electrical contact.

13 Claims, 7 Drawing Sheets

(56)                  References Cited

U.S. PATENT DOCUMENTS

| | | | |
|---|---|---|---|
| 10,726,967 B2 | 7/2020 | Hatakeyama | |
| 11,191,472 B2 | 12/2021 | Shu | |
| 11,642,062 B2 * | 5/2023 | Batzer | A61B 5/25 |
| | | | 600/372 |
| 2011/0279963 A1 | 11/2011 | Kumar | |
| 2016/0361015 A1 * | 12/2016 | Wang | B32B 25/08 |
| 2017/0127969 A1 * | 5/2017 | Su | A61B 5/288 |
| 2021/0259606 A1 * | 8/2021 | Yeo | A61B 5/28 |

* cited by examiner

DRY ELECTRODES FOR ELECTROPHYSIOLOGY MEASUREMENT

BACKGROUND

In the field of electrophysiology, electrodes are used to connect a measurement device with a biological body. These electrodes have an electrode that makes contact with the skin of a body on one side, and a snap on the opposing side for making an electrical connection to an instrument or measurement device used for electrophysiological measurements or monitoring, or both.

One known electrode is a hydrogel electrode. Hydrogel electrodes are used for various electrophysiological measurements, such as electrocardiography (EKG) monitoring, connecting the patient to a patient monitor. Disposable hydrogel electrodes are also used for impedance measurements (for respiratory activity and stress), electromyography for muscle activity measurements and electroencephalography (EEG) for brain activity measurements.

Known dry electrodes require a small amount of moisture (e.g., perspiration) in between the electrode and the skin for the electrode to function well. Unfortunately, too much moisture can build up between the electrode and the skin, especially when the electrode is worn for long term wear (e.g., three or more days). This excessive moisture can result in poor connection of the electrode to the skin, an addition of an undesired insulating water-contacting layer, detachment of the electrode from the skin, and colorization of skin.

What is needed, therefore, is an apparatus for making contact to the skin for electrophysiological measurements and monitoring that at least the drawbacks of known electrodes described above.

SUMMARY

According to an aspect of the present disclosure, an apparatus for making electrical connections in electrophysiological measurements and monitoring is disclosed. The apparatus comprises: a first side comprising an electrical contact; a second side opposing the first side comprising an electrode disposed over the second side; and a layer disposed between the first side and the second side. The layer is adapted to remove moisture from a region around the electrode. The apparatus further comprises an electrode line in electrical contact with the electrode disposed over the layer on the first side and extending over the layer on the second side, wherein the electrode line is electrically connected to the electrical contact.

According to another aspect of the present disclosure, an apparatus for making electrical connections in electrophysiological measurements and monitoring is described. The apparatus comprises: a first side comprising an electrical contact; and a second side opposing the first side comprising an electrode disposed over the second side. The electrode comprises a groove adapted to remove moisture from a region around the electrode.

According to another aspect of the present disclosure, an apparatus for making electrical connections in electrophysiological measurements and monitoring is disclosed. The apparatus comprises: a first side comprising an electrical contact; a second side opposing the first side comprising an electrode disposed over the second side; a layer comprising a gap and being disposed between the first side and the second side, wherein the gap is adapted to remove moisture from a region beneath the electrical contact; and a plurality of electrically conductive spokes extending radially from an outer boundary of the electrical contact.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
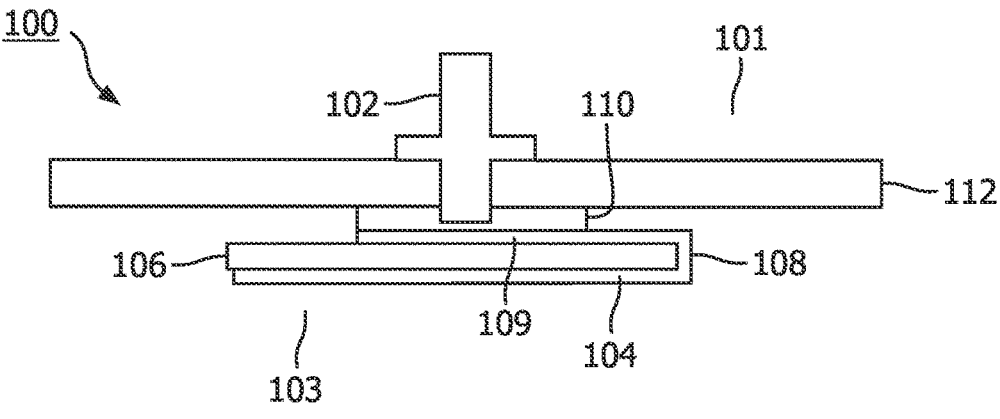
FIG. 1A is a cross-sectional view of an apparatus for making electrical connections in electrophysiological measurements and monitoring according to a representative embodiment.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

By the present teachings, among other things, apparatuses for making electrical connections in electrophysiological measurements and monitoring are disclosed. As described more fully below, in certain embodiments a layer is provided between the electrical contact and the electrode. In other embodiments, a groove is provided in the electrode. In yet other embodiments, a layer comprising a gap and is disposed between the first side and the second side of the apparatus, and a plurality of electrically conductive spokes extend radially from an outer boundary of the electrical contact. Among other benefits and improvements to the technical field, the various representative embodiments provide various ways to remove moisture between the electrode adapted to contact the surface (e.g., skin) of a body. This removal of moisture improves not only the electrical connections between the measurement or monitor devices, but also improves the duration of the adhesion of the apparatus to the body and prevents irritation of the body at the location of the electrode to the skin.

Turning to FIG. 1A, a cross-sectional view of an apparatus 100 for making electrical connections in electrophysiological measurements and monitoring is disclosed. The apparatus 100 comprises a first side 101 comprising an electrical contact 102 having a contacting portion; a second side 103 opposing the first side 101 and comprising an electrode 104 disposed over the second side 103. A layer 106 is disposed between the first side 101 and the second side 103 which makes contact with the body (e.g., the skin of the body). As described more fully below, the layer 106 is adapted to remove moisture from a region around the electrode 104 where the electrode 104 contacts the body.

The apparatus 100 further comprises an electrode lead line 108 disposed over the layer 106 on the second side 103 and extending over the layer 106 on the first side 101 and provides an electrical connection between the electrode 104 and the electrical contact 102 at an opposing electrical contact 109 via a contacting portion 110 of the electrical contact 102. Notably, the electrode lead line 108 (and similar lead lines described herein) may comprise a single layer of electrical conductive material directly applied (e.g., printed) on layer 106, or may comprise a "free-standing" a layer of electrical conductive material disposed on a substrate. Finally, the apparatus 100 comprises an adhesive layer 112 that affixes the apparatus to the body. Notably, adhesive layer 112 also comprises a backing layer (not shown) facing the first side 101 (i.e., the side opposing the side of adhesive layer 112 opposing the adhesive layer). The backing layer may comprise foil, foam, paper, woven knitted textiles, or non-woven knitted textiles.

In operation, the apparatus 100 is adhered to the body by the adhesive layer 112 with the electrode 104 making physical contact to the body. The electrode lead line 108 provides an electrical connection between the electrode 104 and the electrical contact 102, which is illustratively a snap contact that connects to lead from a measurement or monitoring device (not shown).

The layer 106 is not substantially electrically conductive, but substantially electrically insulative, and is selected for its ability its remove moisture in the region where the electrode 104 contacts the body at the second side. Illustratively, layer 106 has a resistance that is greater than that of human skin (i.e., greater than 0.1M $\Omega$ to 1.0 M$\Omega$). Notably, while the layer 106 could be electrically conductive, the materials selected for this layer are selected for their moisture removal properties. Many if not all of such materials are not electrically conductive. Generally, the layer 106 comprises a porous biocompatible material that can absorb and/or transport moisture in the region where the electrode 104 makes contact with the body converts and transports the bio-signals (as e.g. EKG) to the electrode lead line 108, but releases the moisture to the ambient. Beneficially, the layer 106 is a breathable that transports humidity and gases/air and thus wicks moisture from the region where the electrode 104 makes contact with the body and substantially reduces or prevents collection of moisture in the region where the electrode 104 makes contact with the body (i.e., between the electrode 104 and the body). In certain representative embodiments, the layer 106 comprises an open cell foam material that is breathable and beneficially exhibits moisture removal from the region where the electrode makes contact with the body. Notably, open cell foam is a synthetic foam in which all air pockets are not completely enclosed and have a 'cobweb' or 'lattice' structure appearance. The open cell foam contemplated for use as the layer 106 is soft and flexible compared to known materials used in wound care. Selected open cell foam materials contemplated for use as the layer 106 allow water/sweat to flow between the air pockets, and ultimately and beneficially out of the region where the electrode 104 makes contact with the body. The layer 106 having an open cell foam structure has a thickness that is great enough to allow moisture to pass through it (as opposed to tape, which does not).

Illustratively, open cell foam from Yulex® Incorporated of Chandler, AZ USA, such as Yulex® OC foam, may be used for the layer 106.

Figure 1B:
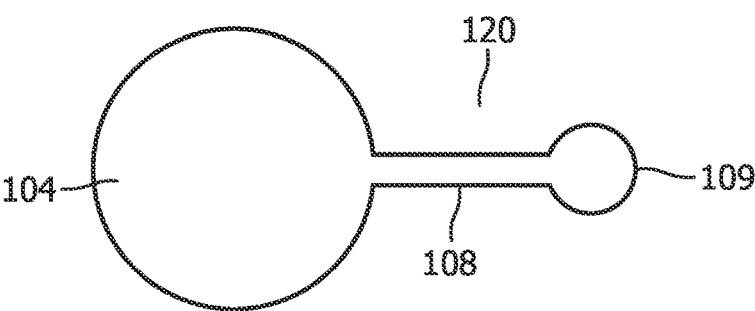
FIG. 1B is top view of an electrode structure for use in an apparatus for making electrical connections in electrophysiological measurements and monitoring according to a representative embodiment.

FIG. 1B is top view of an electrode structure 120 for use in the apparatus 100 for making electrical connections in electrophysiological measurements and monitoring according to a representative embodiment. Various aspects and details of the presently described representative embodiments are common to those described above in connection with FIG. 1A, and may not be repeated to avoid obscuring the presently described representative embodiments. The electrode structure 120 comprises the electrode 104, the opposing electrical contact 109, and the electrode lead line 108 disposed therebetween. The electrode structure 120 may comprise a known biocompatible electrically conductive material used in medical applications. By way of illustration, the biocompatible electrically conductive material used for the electrode structure 120 may be as described in U.S. Pat. Nos. 8,792,957, 10,726,967, and U.S. Patent Application Publication No. 2021/0386379. As shown more clearly in FIG. 1A, the electrode lead line 108 is disposed (e.g., folded) around the layer 106 and provides an electrical path between the electrode 104 and the electrical contact 102 via the opposing electrical contact 109.

Notably, the electrode structure 120 may be an integral unit as shown formed from a piece of suitably electrically conductive material. Alternatively, the electrode 104 may be connected to the opposing electrical contact 109 via an electrically conductive line printed on the layer 106 and between the electrode 104 and the opposing electrical contact. Illustratively, the printed electrically conductive line may comprise a layer of silver chloride (AgCl) over a layer of silver disposed over the layer 106 using one of a variety of known techniques.

Figure 1C:
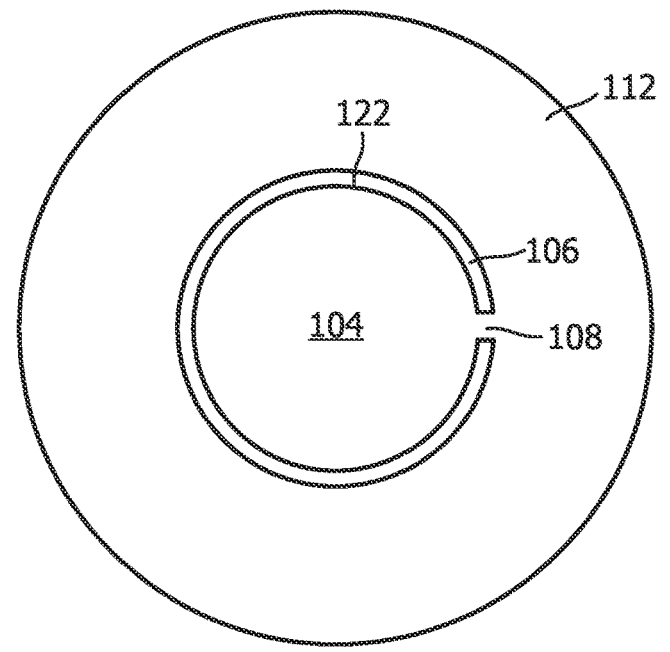
FIG. 1C is top view of an apparatus for making electrical connections in electrophysiological measurements and monitoring according to a representative embodiment.

FIG. 1C is top view of apparatus 100 for making electrical connections in electrophysiological measurements and monitoring according to a representative embodiment. Notably, FIG. 1C depicts the apparatus 100 from the second side 103, which is the side of the apparatus that makes contact with the body. Various aspects and details of the presently described representative embodiments are common to those described above in connection with FIGS. 1A-1B, and may not be repeated to avoid obscuring the presently described representative embodiments.

As shown, the apparatus 100 comprises the electrode 104 that makes contact with the body, and the adhesive layer 112 that provides the adhesion of the apparatus 100 to the body. Also shown are the portion of layer 106 that extends past an edge 122 of the electrode 104, and the electrode lead line 108 that is folded or otherwise disposed over the side of layer 106 and provides the electrical connection between the electrode 104 and the electrical contact 102 (not shown in FIG. 1C) of the apparatus. As noted above, the layer 106 wicks moisture from the region where the electrode 104 makes contact with the body and past the edge 122 of the electrode 104 for removal into the ambient. This action by the layer substantially reduces or prevents collection of moisture in the region where the electrode 104 makes contact with the body (i.e., between the electrode 104 and the body). Again, in certain representative embodiments, the layer 106 comprises an open cell foam material that is breathable and beneficially exhibits moisture removal from the region where the electrode 104 makes contact with the body.

FIGS. 2A-2D are top views of electrode structures 220 for use in apparatuses for making electrical connections in electrophysiological measurements and monitoring according to a representative embodiment. Various aspects and details of the presently described representative embodiments are common to those described above in connection with FIGS. 1A-1C, and may not be repeated to avoid obscuring the presently described representative embodiments. Notably, the electrode structures 220 comprise an electrically conductive material as noted above, and have the layer 106 (not shown in FIGS. 2A-2D) and the adhesive layer 112 (not shown in FIGS. 2A-2D) disposed thereover. As such, the electrode structures 220 are similar to the electrode structure 120 described in connection with FIGS. 1B-1C with modifications discussed presently.

Improving the surface area of contact between the layer 106 and the body to which the apparatus 100 is attached beneficially increases the ability of the layer 106 to remove moisture from the region where the electrode makes contact with the body. FIGS. 2A-2D depict illustrative electrode structures 220 each comprising an electrode 204, and an electrical line 208 making an electrical connection between the electrode 204 and the opposing electrical contact 209. However, the electrodes 204 of the electrode structures 220 of FIGS. 2A-2D have portions removed as shown. As will be appreciated, when electrode structures 220 are substituted from electrode structure 120 in the structure such as depicted in FIG. 1A, the portions of the electrodes 204 that are removed have corresponding portions of the layer 106 exposed. By reducing the area of the layer 106 that is covered by the electrodes 204, removal of moisture in the region where the electrode 204 makes contact with the body is improved. While the area of contact for making measurements is reduced with the removal of portions of the electrode 204, the improvement in wearability is beneficial. Stated somewhat differently, layer 106 wicks away moisture via its height towards the outside where this layer 106 is not covered by the contacting portion 110. The grooves of the presently described embodiments enable more efficient transportation of moisture (sweat) by providing a more direct path (moisture does not need to pass through the electrode 104), and by providing a capillary effect to create a channel effect pulling moisture away from the center of the electrode 204. Notably, the grooves may comprise a venus valve.

Specifically, as described above, removal of moisture in the region where the electrodes 104, 204 beneficially results in better adhesion of the electrode 104, 204, reduces skin irritation from prolonged wear, and results in better performance of the electrodes 104, 204. Furthermore, the various openings in the electrode structure discussed below, foster improved mobility of the electrodes 104, 204. Specifically, the electrodes 104, 204 are elastic and follow the movements of the skin. By removing portions of the electrode such as the grooves and openings of electrode 204 described below, the electrode 204 is more pliable than electrode 104 described above. This increase in pliability allows the electrode 204 to move more freely with movement of the anatomical part of the body to which it is attached, resulting in a more comfortable connection with a reduction in its becoming unattached from the body. So, in addition to providing an improvement in moisture removal, the grooves and openings described below further improve the long-term performance of the electrode structures of various representative embodiments.

Figure 2A:
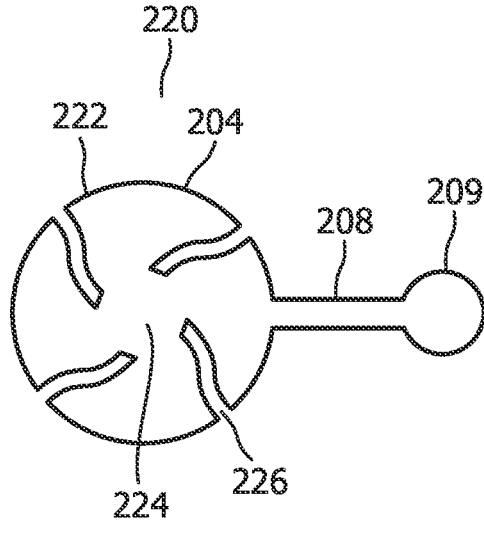
FIGS. 2A-2D are top views of electrode structures for use in apparatuses for making electrical connections in electrophysiological measurements and monitoring according to a representative embodiment.

FIG. 2A shows a top view of the electrode structures 220 comprising the electrode 204, and the electrical line 208 making an electrical connection between the electrode 204 and an opposing electrical contact 209. In the electrode structure 220 of FIG. 2A, a central portion 224 and grooves 226 extending therefrom are formed by removal of the electrode 204 (or just not forming the electrode 204 in the central portion 224 and grooves 226) as shown. In the electrode structure 220 of FIG. 2A, with the central portion 224 and the grooves 226, when substituted for electrode 104 in the apparatus 100 described above, expose more surface area of the layer 106 to the ambient, thereby fostering improved removal of moisture from the region where the electrode 204 makes contact with the body. Furthermore, in addition to exposing the layer 106 (not shown in FIG. 2A), the grooves 226 also provide paths for the moisture to be removed from an edge 222 of the electrode 204. As such, the grooves provide a capillary action, which results in further removal of moisture from the region where the electrode 204 makes contact with the body.

Figure 2B:
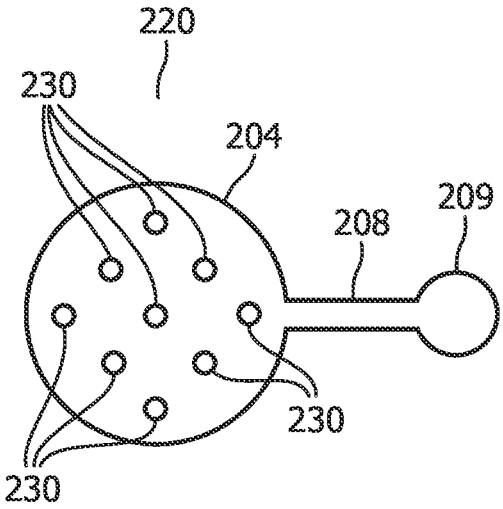

FIG. 2B shows a top view of the electrode structure 220 comprising the electrode 204, and the electrical line 208 making an electrical connection between the electrode 204 and the opposing electrical contact 209. In the electrode structure 220 of FIG. 2B, a openings 230 are provided in the electrode 204 and thereby, when substituted for electrode 104 in the apparatus 100 described above, exposes more surface area of the layer 106 to the ambient, thereby fostering improved removal of moisture from the region where the electrode 204 makes contact with the body.

Figure 2C:
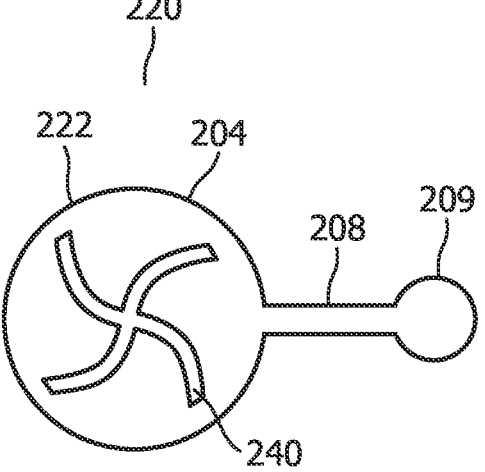

FIG. 2C shows a top view of the electrode structures 220 comprising the electrode 204 and the electrical line 208 making an electrical connection between the electrode 204 and the opposing electrical contact 209. In the electrode structure 220 of FIG. 2C, grooves 240 extend from the center of the electrode 204 by removal of the electrode 204 (or just not forming the electrode 204 where grooves 226 are provided) as shown. In the electrode structure 220 of FIG. 2C, with the grooves 226, when substituted for electrode 104 in the apparatus 100 described above, more surface area of the layer 106 is exposed to the ambient, thereby fostering improved removal of moisture from the region where the electrode 204 makes contact with the body. Furthermore, in addition to exposing the layer 106 (not shown in FIG. 2C), the grooves 240 provide paths for the moisture to be removed toward the edge 222 of the electrode 204. This improves further removal of moisture from the region where the electrode 204 makes contact with the body.

Figure 2D:
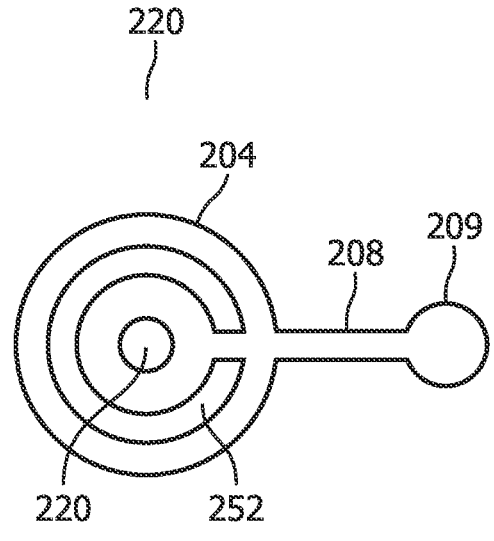

FIG. 2D shows a top view of the electrode structure 220 comprising the electrode 204, and the electrical line 208 making an electrical connection between the electrode 204 and the opposing electrical contact 209. In the electrode structure 220 of FIG. 2D, a central portion 250 and a surrounding portion 252 are provided in the electrode 204 by removing or not forming the electrode 204 in these areas. When substituted for electrode 104 in the apparatus 100 described above, more surface area of the layer 106 is exposed to the ambient, thereby fostering improved removal of moisture from the region where the electrode 204 makes contact with the body.

Figures 3A, 3B:
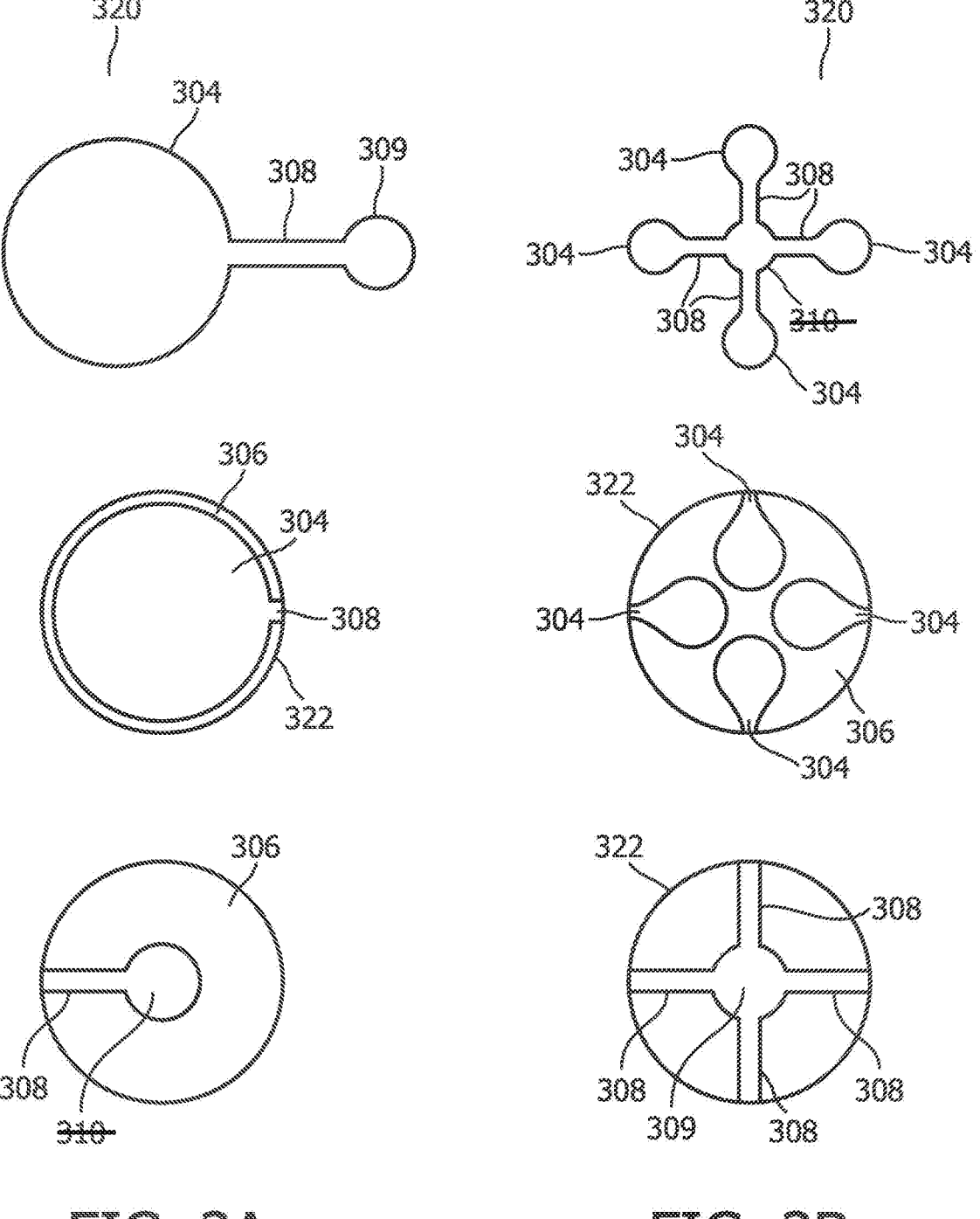
FIGS. 3A-3C are top views of electrodes, electrical contacts, electrode lines and layers adapted to remove moisture from a region around the electrode according to various representative embodiments.
Figure 3C:
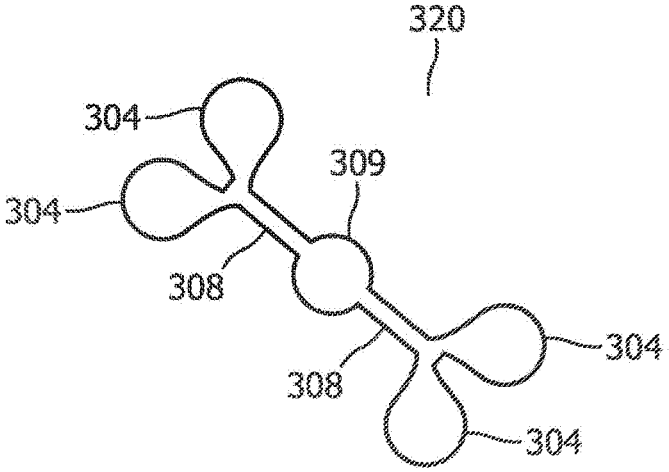
Figure 3C:
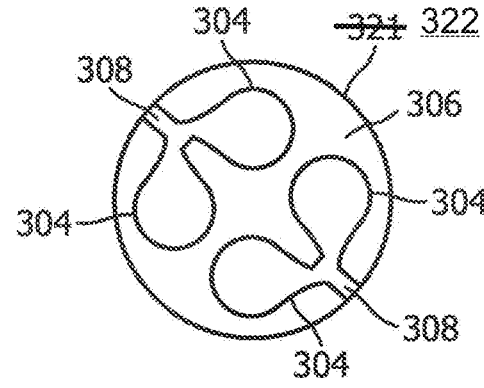
Figure 3C:
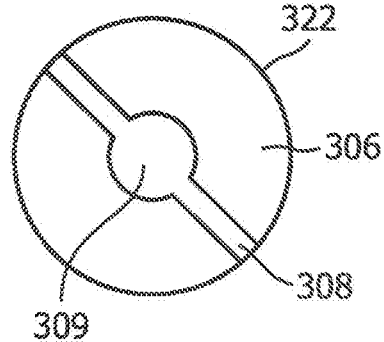

FIGS. 3A-3C are top views of electrodes, electrical contacts, electrode lines, and layers adapted to remove moisture from a region around the electrode according to various representative embodiments. Various aspects and details of the presently described representative embodiments are common to those described above in connection with FIGS. 1A-2D, and may not be repeated to avoid obscuring the presently described representative embodiments.

Turning to top part of FIG. 3A an electrode structure 320 is shown, and comprises an electrode 304 and an opposing electrical contact 309 connected to the electrode 304 by an electrical lead line. As will be appreciated, the electrode 304 is disposed on the second side and is in contact with the body, whereas the opposing electrical contact 309 is on the first side and makes electrical contact with the electrical contact 102 shown in FIG. 1. As will be appreciated, the electrode structure 320 is substantively the same as electrode structure 120 discussed above in connection with FIG. 1B.

In the middle part, FIG. 3A also shows a portion of layer 306 that extends past an edge 322 of the electrode 304, and the electrode lead line 308 that is folded or otherwise disposed over the side of layer 106 and provides the electrical connection between the electrode 304 and the electrical contact 102 (not shown in FIG. 3A) of the apparatus. Stated somewhat differently, if substituted for the electrode structure 120 of FIG. 1B, this part of FIG. 3A would be on the second side 103 of the apparatus 100. As noted above, the layer 306 wicks moisture from the region where the electrode 304 makes contact with the body and past the edge 322 of the electrode 304 for removal into the ambient.

Finally, in the lower part FIG. 3A shows the layer 306 with the opposing electrical contact 309 and electrode lead line 308. If substituted for the electrode structure 120 of FIG. 1B, this part of FIG. 3A would be on the first side 101 of the apparatus 100, with the opposing electrode making contact with electrical contact 102.

Turning to top part of FIG. 3B an electrode structure 320 is shown, and comprises electrodes 304 and an opposing electrical contact 309 connected to each of the electrodes 304 by respective electrode lead lines 308. As will be appreciated, the electrodes 304 are disposed on the second side and are in contact with the body, whereas the opposing electrical contact 309 is on the first side and makes electrical contact with the electrical contact 102 shown in FIG. 1.

In the middle part, FIG. 3B also shows layer 306 with the electrodes 304, and the electrode lead lines 308 that are folded or otherwise disposed over the side of layer 306 and provides the electrical connection between the respective electrodes 304 and the electrical contact 102 (see FIG. 1A—not shown in FIG. 3B) of the apparatus. Stated somewhat differently, if substituted for the electrode structure 120 of FIG. 1B, this part of FIG. 3B would be on the second side 103 of the apparatus 100. As noted above, the layer 306 wicks moisture from the region where the electrodes 304 makes contact with the body and past the edge 322 of the electrode 304 for removal into the ambient. Notably, however, compared to the representative embodiment of FIG. 3A, a greater surface area of the layer 306 is exposed and thus is in contact with the skin and fosters more efficient removal of moisture from the region where the electrodes 304 make contact with the body. While the area of contact for making measurements is reduced using electrodes 304 in FIG. 3B, the improvement in wearability is beneficial. Specifically, as described above, removal of moisture in the region where the electrodes 304 beneficially results in better adhesion of the electrodes 304 and reduces skin irritation from prolonged wear.

Finally, in the lower part FIG. 3B shows the layer 306 with the opposing electrical contact 309 and electrode lead lines 308 that connect the opposing electrical contact 309 to electrodes 304. If substituted for the electrode structure 120 of FIG. 1B, this part of FIG. 3B would be on the first side 101 of the apparatus 100, with the opposing electrode making contact with electrical contact 102. Furthermore, compared to the structure of FIG. 3A, in the electrode structure 320 of FIG. 3B the surface area of the electrodes 304 is reduced. Like the grooves and openings described above in connection with FIGS. 2A-2D, this reduction in contact area of the electrodes 304 with the body not only increases the exposed surface area of the layer 306, but also fosters improved mobility of the electrode structure 320 on side that contacts the body. Specifically, the electrodes 304 are elastic and follow the movements of the skin. By providing a comparative reduction in the area of connection of the electrodes 304 (compared to the electrode 304 of FIG. 3A or electrode 104 of FIG. 1B), the electrode structure 320 is more pliable. This increase in pliability allows the electrode 304 to move more freely with movement of the anatomical part of the body to which it is attached, resulting in a more comfortable connection with a reduction in its becoming unattached from the body. So, in addition to providing an improvement in moisture removal, the grooves and openings described below further improve the long-term performance of the electrode structures of various representative embodiments.

Turning to top part of FIG. 3C an electrode structure 320 is shown, and comprises electrodes 304 and an opposing electrical contact 309 connected to each of the electrodes 304 by respective electrode lead lines 308. As will be appreciated, the electrodes 304 are disposed on the second side and are in contact with the body, whereas the opposing electrical contact 309 is on the first side and makes electrical contact with the electrical contact 102 shown in FIG. 1.

In the middle part, FIG. 3C shows layer 306 with the electrodes 304, and the electrode lead lines 308 that are folded or otherwise disposed over the side of layer 306 and provide the electrical connection between the respective electrodes 304 and the electrical contact 102 (see FIG. 1A—not shown in FIG. 3C) of the apparatus. Stated somewhat differently, if substituted for the electrode structure 120 of FIG. 1B, this part of FIG. 3C would be on the second side 103 of the apparatus 100. As noted above, the layer 306 wicks moisture from the region where the electrodes 304 makes contact with the body and past the edge 322 of the electrode 304 for removal into the ambient. Notably, however, compared to the representative embodiment of FIG. 3A, a greater surface area of the layer 306 is exposed and thus is in contact with the skin, and fosters more efficient removal of moisture from the region where the electrodes 304 make contact with the body. While the area of contact for making measurements is reduced using electrodes 304 in FIG. 3C, the improvement in wearability is beneficial. Specifically, as described above, removal of moisture in the region where the electrodes 304 beneficially results in better adhesion of the electrodes 304 and reduces skin irritation from prolonged wear.

Finally, in the lower part FIG. 3B shows the layer 306 with the opposing electrical contact 309 and electrode lead lines 308 that connect the opposing electrical contact 309 to electrodes 304. If substituted for the electrode structure 120 of FIG. 1B, this part of FIG. 3B would be on the first side 101 of the apparatus 100, with the opposing electrode making contact with electrical contact 102. Furthermore, compared to the structure of FIG. 3A, in the electrode structure 320 of FIG. 3C, the surface area of the electrodes 304 is reduced. Like the grooves and openings described above in connection with FIGS. 2A-2D, this reduction in contact area of the electrodes 304 with the body not only increases the exposed surface area of the layer 306, but also fosters improved mobility of the electrode structure 320 on side that contacts the body. Specifically, the electrodes 304 are elastic and follow the movements of the skin. By providing a comparative reduction in the area of connection of the electrodes 304 (compared to the electrode 304 of FIG. 3A or electrode 104 of FIG. 1B), the electrode structure 320 is more pliable. This increase in pliability allows the electrode 304 to move more freely with movement of the anatomical part of the body to which it is attached, resulting in a more comfortable connection with a reduction in its becoming unattached from the body. So, in addition to providing an improvement in moisture removal, the grooves and openings described below further improve the long-term performance of the electrode structures of various representative embodiments.

Figure 4A:
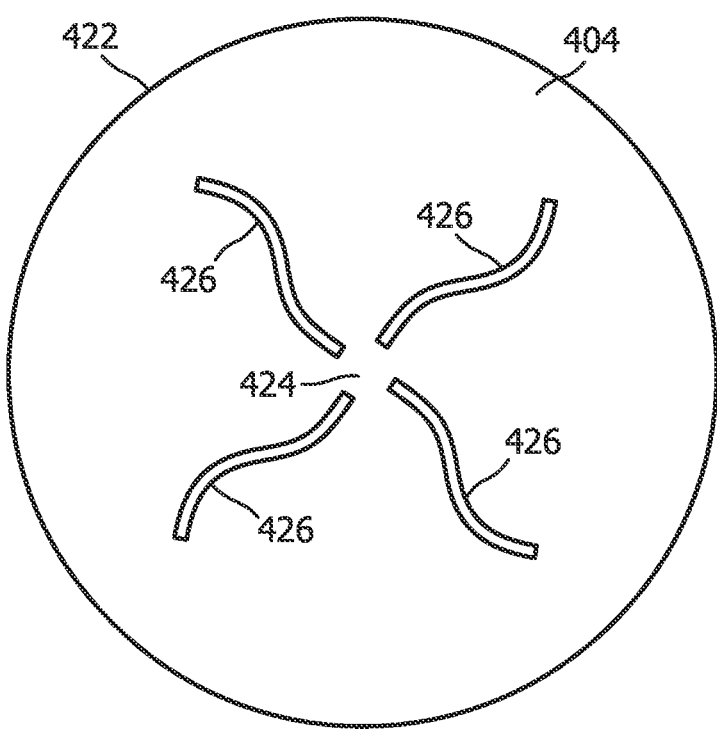
FIGS. 4A-4B are top views of electrodes for use in apparatuses for making electrical connections in electrophysiological measurements and monitoring according to a representative embodiment.
Figure 4B:
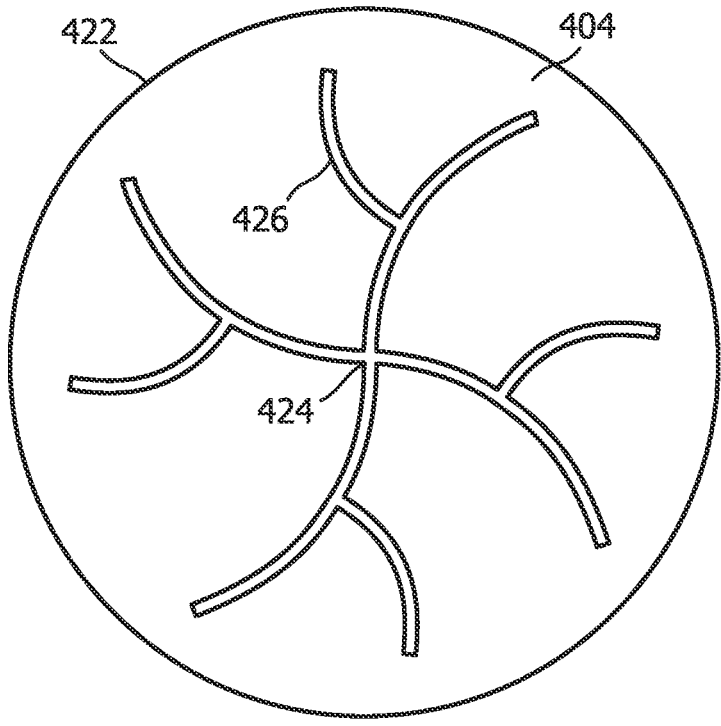

FIGS. 4A-4B are top views of electrodes for use in apparatuses for making electrical connections in electro-physiological measurements and monitoring according to a representative embodiment. Various aspects and details of the presently described representative embodiments are common to those described above in connection with FIGS. 1A-3C, and may not be repeated to avoid obscuring the presently described representative embodiments.

Turning to FIG. 4A, a top view of an electrode 404 is shown. The electrode 404 has grooves 426 extending from a central portion 424. As noted above, the grooves are formed by removal of portions of the electrode 404 (or just not forming the electrode 404 in the regions where the grooves 426 are provided) as shown.

The electrode 404 differs from the previously described electrode structures (e.g., electrode structure 220) at least because no layer (e.g. layer 106) is provided over the electrode 404. Rather, the grooves 426 provide paths for the moisture to be removed toward the edge 422 of the electrode 404. As such, the grooves 426 provide a capillary action, which results in removal of moisture from the region where the electrode 204 makes contact with the body. Notably, the electrode 404 may have grooves/openings such as shown in and described in connection with the representative embodiments of FIGS. 2A-2D.

Another difference between the electrode 404 and the previously described electrode structure is the absence of an electrical line (e.g., electrode lead line 108) and opposing electrical contact (e.g., opposing electrical contact 109). To this end, because a layer (e.g., layer 106) is not used in this representative embodiment, the electrical path that connects the electrode (e.g., 204) to the electrical contact (e.g., electrical contact 102) is not needed. Rather, as described more fully below in connection with FIGS. 5A and 5B, the electrode 404 makes direct contact with the electrical contact to which leads are attached to connect the electrode 404 to the measurement or monitoring device. When substituted for electrode 104 in the apparatus 100 described above, and foregoing the layer 106, electrode lead line 108 and opposing electrical contact 109, moisture is removed by the grooves 426 from the central portion 424 towards the edge 422, thereby fostering improved removal of moisture from the region where the electrode 404 makes contact with the body.

Turning to FIG. 4B, a top view of electrode 404 is shown. The electrode 404 has grooves 426 extending from the central portion 424. As noted above, the grooves are formed by removal of portions of the electrode 404 (or just not forming the electrode 404 in the regions where the grooves 426 are provided) as shown.

The electrode 404 differs from the previously described electrode structures (e.g., electrode structure 220) at least because no layer (e.g. layer 206) is provided over the electrode 404. Rather, the grooves 426 provide paths for the moisture to be removed toward the edge 422 of the electrode 404. As such, the grooves 426 provide a capillary action, which results in removal of moisture from the region where the electrode 204 makes contact with the body.

Another difference between the electrode 404 and the previously described electrode structures is the absence of an electrical line (e.g., electrode lead line 108) and opposing electrical contact (e.g., opposing electrical contact 109). To this end, because a layer (e.g., layer 106) is not used in this representative embodiment, the electrical path (e.g., electrode lead line 108) that connects the electrode (e.g., 204) to the electrical contact (e.g., electrical contact 102) is not needed. Rather, as described more fully below in connection with FIGS. 5A and 5B, the electrode 404 makes direct contact with the electrical contact (e.g., electrical contact 102) to which leads are attached to connect the electrode 404 to the measurement or monitoring device. When substituted for electrode 104 in the apparatus 100 described above, and foregoing the layer 106, electrode lead line 108 and opposing electrical contact 109, moisture is removed by the grooves from the central portion 424 towards the edge 422 allowing the moisture to evaporate more easily, thereby fostering improved removal of moisture from the region where the electrode 404 makes contact with the body.

Figures 5A, 5B:
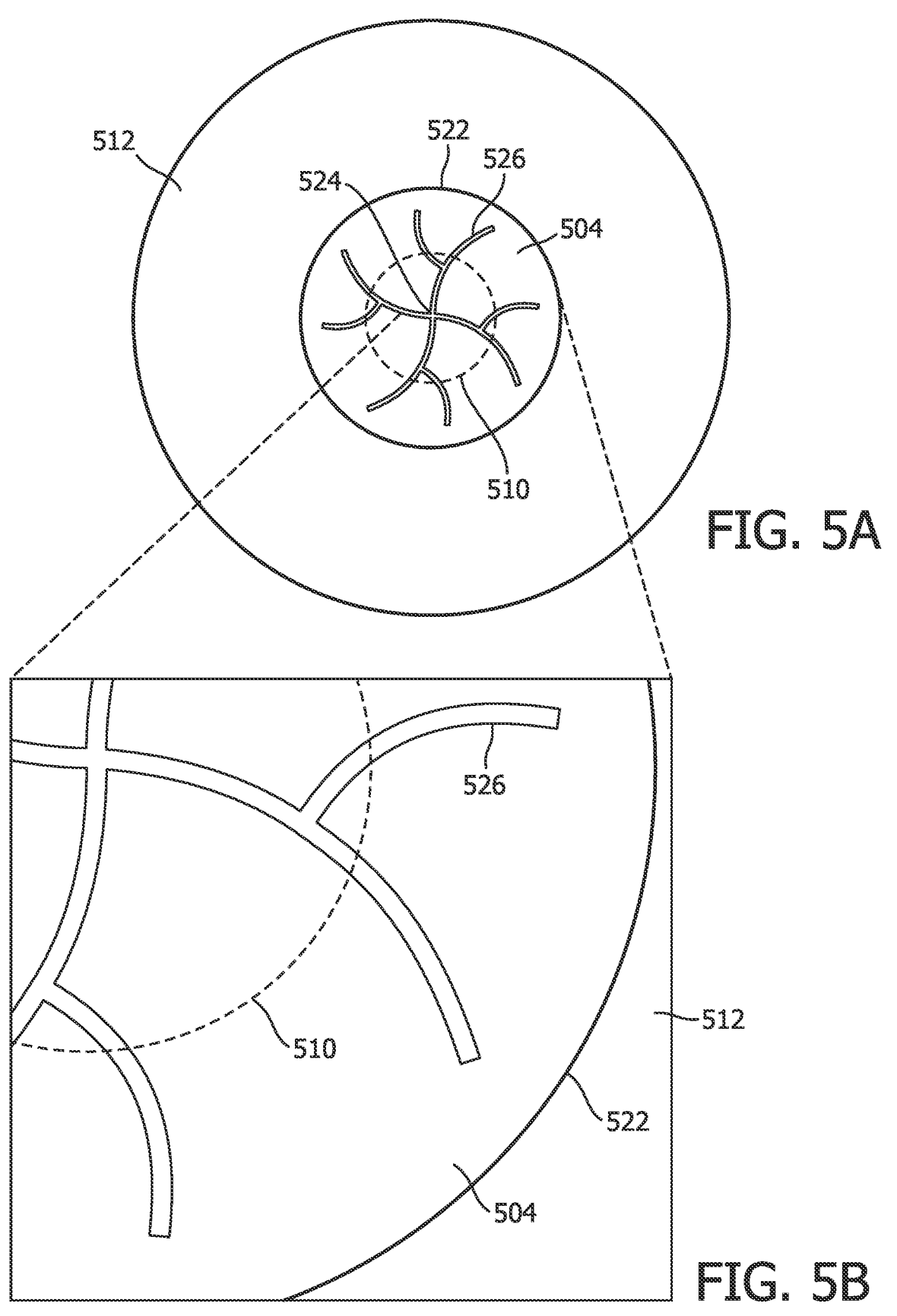
FIG. 5A is a top view of an electrode and an adhesive layer for use in apparatuses for making electrical connections in electrophysiological measurements and monitoring according to a representative embodiment.
FIG. 5B is an enlarged view of a portion of the electrode and adhesive layer of FIG. 5A.

FIG. 5A is a top view of an electrode 504 and an adhesive layer 512 for use in apparatuses for making electrical connections in electrophysiological measurements and monitoring according to a representative embodiment. FIG. 5B is an enlarged view of a portion of the electrode and adhesive layer of FIG. 5A. Various aspects and details of the presently described representative embodiments are common to those described above in connection with FIGS. 1A-4B, and may not be repeated to avoid obscuring the presently described representative embodiments.

Turning to FIG. 5A, the top view of the electrode 504 shows the second side which contacts the skin of the body, and is electrically connected to the electrical contact on the opposing side (e.g., electrical contact 102 on first side 101—not shown in FIG. 5A).

The electrode 504 has grooves 526 extending from central portion 524. As noted above, the grooves 526 are formed by removal of portions of the electrode 504 (or just not forming the electrode 504 in the regions where the grooves 526 are provided) as shown.

The electrode 504 differs from the previously described electrode structures (e.g., electrode structure 220) at least because no layer (e.g. layer 206) is provided over the electrode 404. Rather, the grooves 526 provide paths for the moisture to be removed toward the edge 522 of the electrode 504. As such, the grooves 526 provide a capillary action, which results in removal of moisture from the region where the electrode 504 makes contact with the body allowing the moisture to evaporate more easily.

Another difference between the electrode 504 and the previously described electrode structures is the absence of an electrical line (e.g., electrode lead line 108) and opposing electrical contact (e.g., opposing electrical contact 109). To this end, because a layer (e.g., layer 106) is not used in this representative embodiment, the electrical path (e.g., electrode lead line 108) that connects the electrode (e.g., 104) to the electrical contact (e.g., electrical contact 102) is not needed. Rather, the electrode 504 makes direct contact with the electrical contact, to which leads are attached to connect the electrode 504 to the measurement or monitoring device, via contacting portion (e.g., the electrical connection is made to the electrical contact 102 via the contacting portion 110).

When substituted for electrode 104 in the apparatus 100 described above, and foregoing the layer 106, electrode lead line 108 and opposing electrical contact 109, moisture is removed by the grooves from the central portion 524 and contacting portion (e.g., contacting portion 110 (not shown in FIG. 5A)) on the opposing side (outlined by dotted line 510) towards the edge 522, thereby fostering improved removal of moisture from the region where the electrode 504 makes contact with the body. This is shown more clearly in FIG. 5B. Notably that the moisture only must be transported away from the area where the electrode 504 overlaps the contacting portion. As such, outside the circle formed by the dotted line 510 (and thus outside the contacting portion), the adhesive layer 512 and supporting structure (e.g., a nonwoven fabric or foam) the material can breathe, transporting moisture through the layers.

Figure 6A:
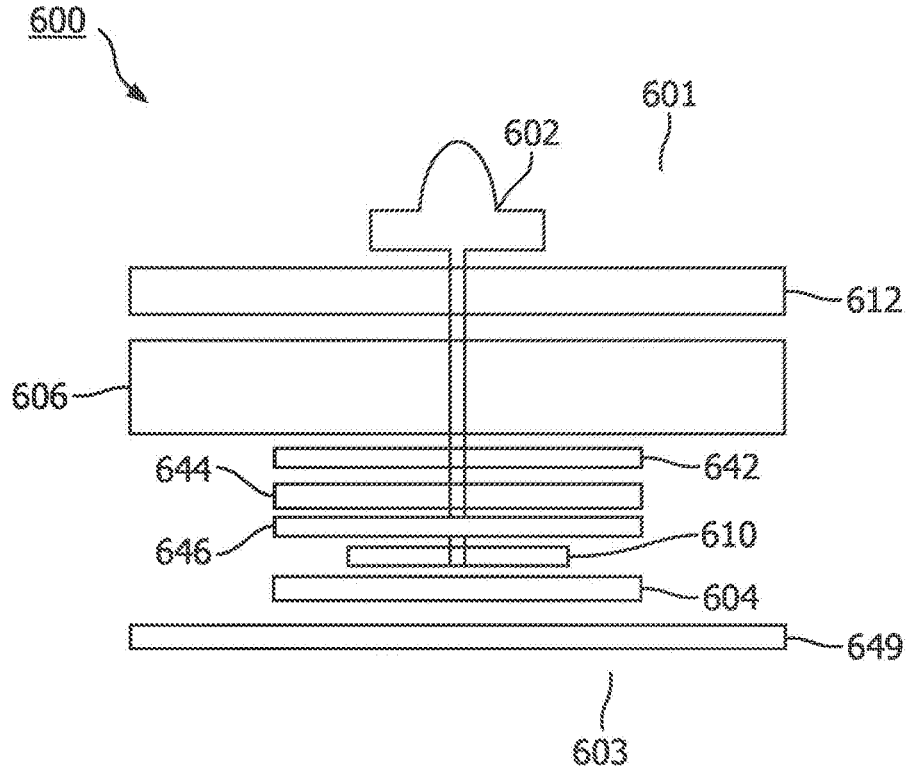
FIG. 6A is a cross-sectional view of an apparatus for making electrical connections in electrophysiological measurements and monitoring according to a representative embodiment.

FIG. 6A is a cross-sectional view of an apparatus 600 for making electrical connections in electrophysiological measurements and monitoring according to a representative embodiment. Various aspects and details of the presently described representative embodiments are common to those described above in connection with FIGS. 1A-5B, and may not be repeated to avoid obscuring the presently described representative embodiments.

Turning to FIG. 6A, a cross-sectional view of an apparatus 600 for making electrical connections in electrophysiological measurements and monitoring is disclosed. The apparatus 100 comprises a first side 601 comprising an electrical contact 602 having a contacting portion 610; and a second side 603 opposing the first side 601 and comprising an electrode 604. A layer 606 is disposed between the first side 601 and the second side 603, which makes contact with the body (e.g., the skin of the body). The layer 606 may be a non-woven material or foam is adapted to remove moisture from a region around the contacting portion 610 where the contacting portion 610 contacts the body. Notably, contacting portion 610 is ring-shaped with an opening in its center.

The apparatus 600 further comprises electrode lead lines 608 (see FIG. 6B), in the shape of spokes and extending over the layer 606 on the first side 601. The electrode lead lines 608 provide an electrical connection between the electrode 604 and the electrical contact 602.

The apparatus 600 further comprises an adhesion layer 642 disposed over an optional foam layer 644 and a conductor 646, which is illustratively printed. The contacting portion 610, which as noted above is ring-shaped, makes electrical contact to the conductor 646 at the center of the electrical contact 602 to ensure electrical contact to the electrode lead lines 608 (spokes). It is beneficial for the contacting portion 610 to make good contact with the conductor 646 to ensure proper conduction of electrical signals (e.g., ECG signals) to the snap. In one representative embodiment, the contacting portion 610 has an outer geometry (e.g., diameter) that is less than or equal to the outer geometry (e.g., diameter) of the conductor 646.

The conductor 646 illustratively comprises spokes, and may be substantially identical in shape to the electrical contact 602 and electrode lead lines 608. This is merely illustrative as the conductor 646 may have shapes of electrodes 204, 304 described in connection with FIGS. 2A-4B. Regardless of the selected shape of the conductor 646, there must be overlap of the contacting portion 610, which is illustratively ring-shaped, and the electrical lead layer 646.

Finally, the apparatus 600 comprises an adhesive layer 612 that affixes the apparatus to the body and a release liner 649 (not shown in FIGS. 1A-5B) that is removed so the apparatus 600 can be applied to the body.

In operation, the apparatus 600 is adhered to the body by adhesive disposed over the electrode 604 making physical contact to the body via the adhesive layer 612. The electrode lead lines 608 provide an electrical connection between the electrode 604 and the electrical contact 602, which is illustratively a snap contact that connects to lead from a measurement or monitoring device (not shown).

Beneficially, the layer 606 is a breathable material wicks moisture from the region where the electrode 604 makes contact with the body and substantially reduces or prevents collection of moisture in the region where the electrode 104 makes contact with the body (i.e., between the electrode 604 and the body).

In certain representative embodiments, the layer 606 and the optional foam layer 644 comprise an open cell foam material that is breathable and beneficially exhibits moisture removal from the region where the electrode makes contact with the body. Notably, open cell foam is a synthetic foam in which all air pockets are not completely enclosed and have a 'cobweb' or 'lattice' structure appearance. The open cell foam contemplated for use as the layer 606 and the optional foam layer 644 are soft and flexible compared to known materials used in wound care. Selected open cell foam materials contemplated for use as the layer 606 (and optional foam layer 644) are not substantially moisture (e.g., water, sweat) resistant allowing water to flow between the air pockets, and ultimately and beneficially out of the region where the electrode 104 makes contact with the body. Illustratively, open cell foam from Yulex® Incorporated of Chandler, AZ USA, such as Yulex® OC foam, may be used for the layer 106. Finally, the optional foam layer 644 may be foregone because it is not necessary to provide an electrode lead line (e.g., 108) over an edge of the foam layer.

Figure 6B:
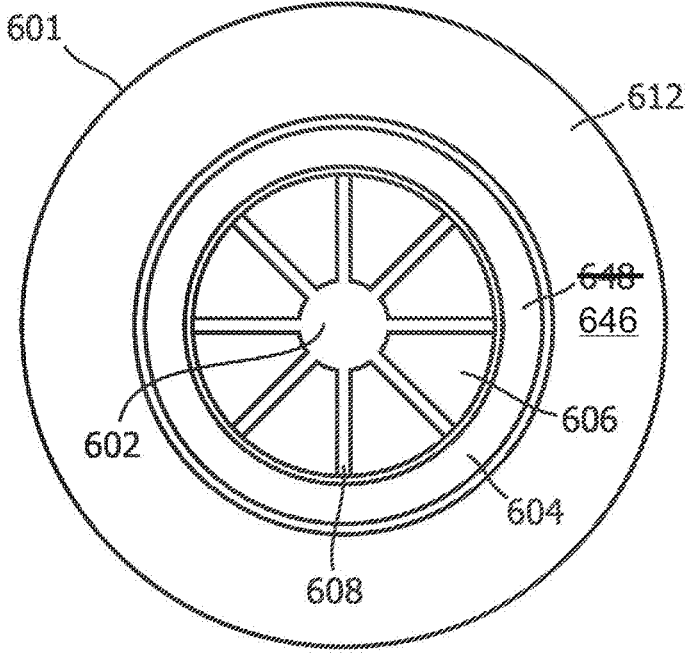
FIG. 6B is top view of an electrode for use in an apparatus for making electrical connections in electrophysiological measurements and monitoring according to a representative embodiment.

FIG. 6B is top view of an electrode for use in an apparatus for making electrical connections in electrophysiological measurements and monitoring according to a representative embodiment. Various aspects and details of the presently described representative embodiments are common to those described above in connection with FIGS. 1A-5B, and may not be repeated to avoid obscuring the presently described representative embodiments.

FIG. 6B is top view of the apparatus 600 shown in FIG. 6A for making electrical connections in electrophysiological measurements and monitoring according to a representative embodiment. Various aspects and details of the presently described representative embodiments are common to those described above in connection with FIG. 1A, and may not be repeated to avoid obscuring the presently described representative embodiments.

The spoke-like structure of the electrode lead lines 608 increase the surface area of layer 606 that is exposed to the ambient. Moreover, as noted above, the electrode 604 may be spoke-like or may have the shape of electrodes 204, 304, 404 as shown in FIGS. 2A-4B, or may have the same shape as the electrode lead lines 608 and electrical contact 602. This structure also fosters improved mobility of the electrode 604 on the side that contacts the body. Specifically, the electrode 604 are elastic and follow the movements of the skin. By providing a comparative reduction in the area of connection of the electrode 604 (compared, for example, to the electrode 304 of FIG. 3A or electrode 104 of FIG. 1B), the electrode structure in FIG. 6B is more pliable. This increase in pliability allows the electrode structure in FIG. 6B to move more freely with movement of the anatomical part of the body to which it is attached, resulting in a more comfortable connection with a reduction in its becoming unattached from the body. So, in addition to providing an improvement in moisture removal, the grooves and openings described below further improve the long-term performance of the electrode structures of various representative embodiments.

Although a variety of apparatuses for making electrical connections to measurement and monitoring devices in electrophysiological measurements and monitoring have been described with reference to several exemplary embodiments, it is understood that the words that have been used are words of description and illustration, rather than words of limitation. Changes may be made within the purview of the appended claims, as presently stated and as amended, without departing from the scope and spirit of interventional procedure optimization in its aspects.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

Although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An apparatus for making electrical connections in electrophysiological measurements and monitoring, the apparatus comprising:
   a first side comprising an electrical contact;
   a second side opposing the first side, the second side comprising an electrode;

a layer disposed between the first side and the second side and adapted to remove moisture from a region of the second side;

an adhesive layer disposed over the layer and configured to affix the apparatus to a body of a user; and a conductive structure comprising a first portion, forming the electrode, and a second portion, forming an opposing electrical contact, the two portions integrally connected by an electrode lead line, wherein the conductive structure is wrapped around the layer such that the first portion is configured to contact skin, and such that the second portion of the conductive structure contacts the electrical contact, wherein the electrode lead line is disposed over the layer on the first side and extends over the layer on the second side so as to be wrapped around an outer edge of the layer, and wherein the opposing electrical contact of the conductive structure is electrically connected to a contacting portion of the electrical contact, such that the electrode lead line provides an electrical connection between the electrode and the opposing electrical contact.

2. The apparatus of claim 1, wherein the layer is configured to contact skin.

3. The apparatus of claim 2, wherein openings exist in the electrode, the openings being adapted to allow the layer to contact the skin.

4. The apparatus of claim 2, wherein an area of the layer configured to contact the skin has a greater magnitude than the electrode configured to contact the skin.

5. The apparatus of claim 2, wherein the layer comprises a biocompatible material.

6. The apparatus of claim 2, wherein the layer comprises an open cell foam material.

7. The apparatus according to claim 1, wherein the electrode comprises a groove adapted to remove moisture from a region around the electrode.

8. The apparatus of claim 7, wherein the groove provides a capillary action.

9. The apparatus of claim 7, wherein the groove comprises a valve.

10. The apparatus of claim 7, wherein the second side is configured to contact skin.

11. The apparatus of claim 10, wherein the electrical contact comprises an area and the groove extends past a boundary of the area.

12. The apparatus of claim 10, wherein the groove is one of a plurality of grooves on the second side.

13. The apparatus of claim 12, wherein the plurality of grooves is in a pattern to facilitate removing of the moisture from the region around the electrode.

\* \* \* \* \*